US010836872B2

(12) United States Patent
Yang et al.

(10) Patent No.: US 10,836,872 B2
(45) Date of Patent: Nov. 17, 2020

(54) VISIBLE LIGHT-CURABLE WATER-SOLUBLE CHITOSAN DERIVATIVE, CHITOSAN HYDROGEL, AND PREPARATION METHOD THEREFOR

(71) Applicant: THE CATHOLIC UNIVERSITY OF KOREA INDUSTRY-ACADEMY COOPERATION, Seoul (KR)

(72) Inventors: Dae Hyeok Yang, Seoul (KR); Heung-Jae Chun, Seoul (KR); Dong In Seo, Seoul (KR)

(73) Assignee: THE CATHOLIC UNIVERSITY OF KOREA INDUSTRY-ACADEMY COOPERATION, Seoul (KR)

( * ) Notice: Subject to any disclaimer, the term of this patent is extended or adjusted under 35 U.S.C. 154(b) by 0 days.

(21) Appl. No.: 16/915,479

(22) Filed: Jun. 29, 2020

(65) Prior Publication Data
US 2020/0325249 A1    Oct. 15, 2020

Related U.S. Application Data

(63) Continuation-in-part of application No. 16/323,634, filed as application No. PCT/KR2017/006393 on Jun. 19, 2017.

(30) Foreign Application Priority Data

Aug. 11, 2016    (KR) .......................... 10-2016-0102602

(51) Int. Cl.
*C08J 3/075*    (2006.01)
*C08J 3/24*    (2006.01)
(Continued)

(52) U.S. Cl.
CPC ............. *C08J 3/075* (2013.01); *A61K 9/0014* (2013.01); *A61K 9/06* (2013.01); *A61K 31/12* (2013.01);
(Continued)

(58) Field of Classification Search
None
See application file for complete search history.

(56) References Cited

U.S. PATENT DOCUMENTS 3,533,940 A    10/1970    Peniston et al.
6,806,260 B1    10/2004    Hirofumi et al.
(Continued)

FOREIGN PATENT DOCUMENTS

JP    4606586 B2    1/2011
KR    10-0546793 B1    1/2006
(Continued)

OTHER PUBLICATIONS

Yoo et al ("A local drug delivery system based on visible light-cured glycol chitosan and doxorubicin.hydrochloride for thyroid cancer treatment in vitro and in vivo", Drug Delivery, vol. 25(1), (2018), p. 1664-1671). (Year: 2018).*
(Continued)

*Primary Examiner* — Sin J Lee
(74) *Attorney, Agent, or Firm* — Sughrue Mion, PLLC

(57) ABSTRACT

A visible light-curable chitosan derivative, a hydrogel thereof, and a preparation method therefor are disclosed. The visible light-curable glycol chitosan derivative is curable by light in the visible light range and has a wound healing activity. A hydrogel obtained by cross-linkage of the visible light-curable glycol chitosan derivative using visible light has a wound healing effect per se, and further, a hydrogel obtained by cross-linkage in a combination of one or more growth factors has an excellent wound healing effect. In addition, a glycol chitosan hydrogel that can prevent the denaturation of contained drugs and growth factors due to the cross-linkage by visible light and is optimized for application to a wet dressing dosage form can be prepared.

17 Claims, 15 Drawing Sheets

(51) Int. Cl.

| | |
|---|---|
| C08J 3/28 | (2006.01) |
| A61K 47/36 | (2006.01) |
| A61K 41/00 | (2020.01) |
| A61K 45/06 | (2006.01) |
| A61K 38/00 | (2006.01) |
| A61K 38/18 | (2006.01) |
| A61K 38/19 | (2006.01) |
| A61K 31/12 | (2006.01) |
| A61K 31/722 | (2006.01) |
| A61K 9/06 | (2006.01) |
| A61K 9/00 | (2006.01) |
| A61L 26/00 | (2006.01) |
| A61P 17/02 | (2006.01) |
| C08B 37/08 | (2006.01) |
| C08K 5/3462 | (2006.01) |

(52) U.S. Cl.
CPC .......... *A61K 31/722* (2013.01); *A61K 38/00* (2013.01); *A61K 38/18* (2013.01); *A61K 38/185* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/193* (2013.01); *A61K 41/00* (2013.01); *A61K 45/06* (2013.01); *A61K 47/36* (2013.01); *A61L 26/008* (2013.01); *A61L 26/0019* (2013.01); *A61L 26/0023* (2013.01); *A61L 26/0066* (2013.01); *A61P 17/02* (2018.01); *C08B 37/003* (2013.01); *C08J 3/24* (2013.01); *C08J 3/28* (2013.01); *A61L 2300/252* (2013.01); *A61L 2300/414* (2013.01); *C08J 2300/14* (2013.01); *C08J 2305/08* (2013.01); *C08J 2471/02* (2013.01); *C08K 5/3462* (2013.01)

(56) References Cited

U.S. PATENT DOCUMENTS

| | | |
|---|---|---|
| 2004/0192646 A1 | 9/2004 | Yura et al. |
| 2010/0291055 A1 | 11/2010 | Athanasiadis et al. |
| 2010/0316715 A1 | 12/2010 | Andersson |
| 2013/0281913 A1 | 10/2013 | Piergallini et al. |
| 2015/0111812 A1* | 4/2015 | Chu .................. A61L 15/28 |
| | | 514/1.1 |

FOREIGN PATENT DOCUMENTS

| | | |
|---|---|---|
| KR | 10-2010-0137146 A | 12/2010 |
| KR | 10-2012-0022383 A | 3/2012 |
| KR | 10-2014-0146813 A | 12/2014 |
| KR | 10-2015-0008858 A | 1/2015 |
| KR | 10-1545506 B1 | 8/2015 |
| KR | 10-1610268 B1 | 4/2016 |
| WO | WO-2019095599 A1 * | 5/2019 ............ A61L 26/00 |

OTHER PUBLICATIONS

Brian G. Amsden et al., "Methacrylated Glycol Chitosan as a Photopolymerizable Biomaterial", Biomacromolecules, Nov. 22, 2007, pp. 3758-3766, vol. 8 No. 12.

Szu-Hsien Chen et al., "Assessment of reinforced poly(ethylene glycol) chitosan hydrogels as dressings in a mouse skin would defect model", Materials Science and Engineering C, Feb. 24, 2013, pp. 2584-2594, vol. 33.

Junli Hu et al., "Visible light crosslinkable chitosan hydrogels for tissue engineering", Acta Biomaterialia, Jan. 30, 2012, pp. 1730-1738, vol. 8.

Eun-Hye Kim et al., "Properties of Photo-Reactive Natural Polymer Derivatives and Its Applications", KIC News, 2015, 10 pages, vol. 18, No. 4.

Titima Songkroh et al., "Injectable In situ Forming Chitosan-Based Hydrogels For Curcumin Delivery", Macromolecular Research, 2015, pp. 53-59, vol. 23, No. 1.

Christopher Kenji Arakawa et al., "A Novel Photopolymerizable Chitosan Collagen Hydrogel for Bone Tissue Engineering", University of California, Biomedical Engineering, 2012, 95 pages.

International Search Report for PCT/KR2017/006393 dated Dec. 4, 2017 [PCT/ISA/210].

* cited by examiner

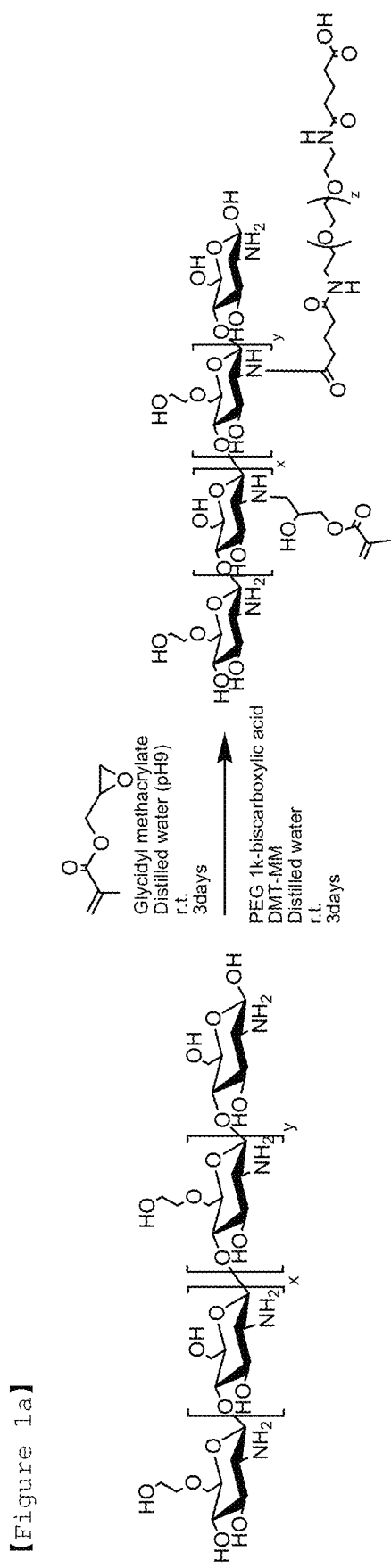
[Figure 1a]

【Figure 1b】
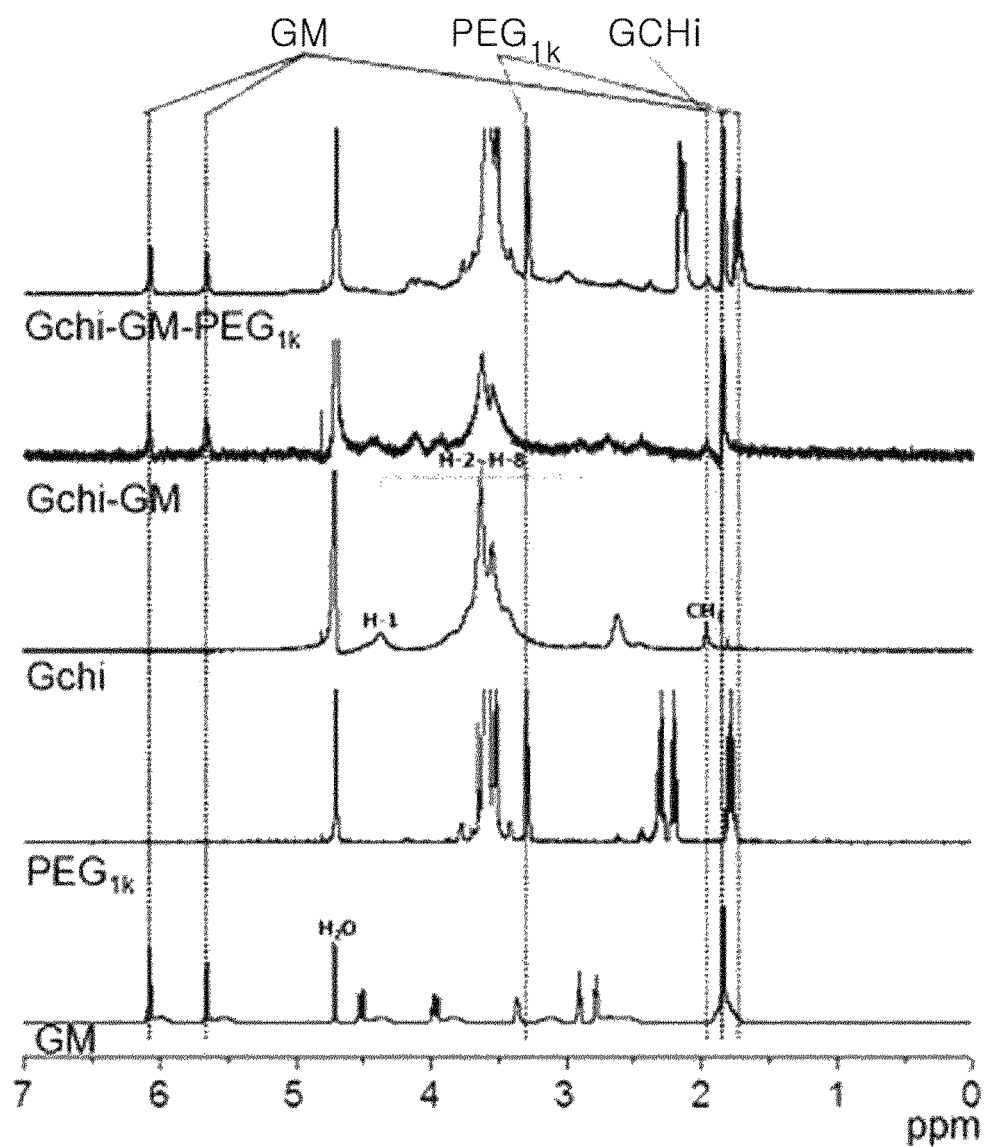

【Figure 2】
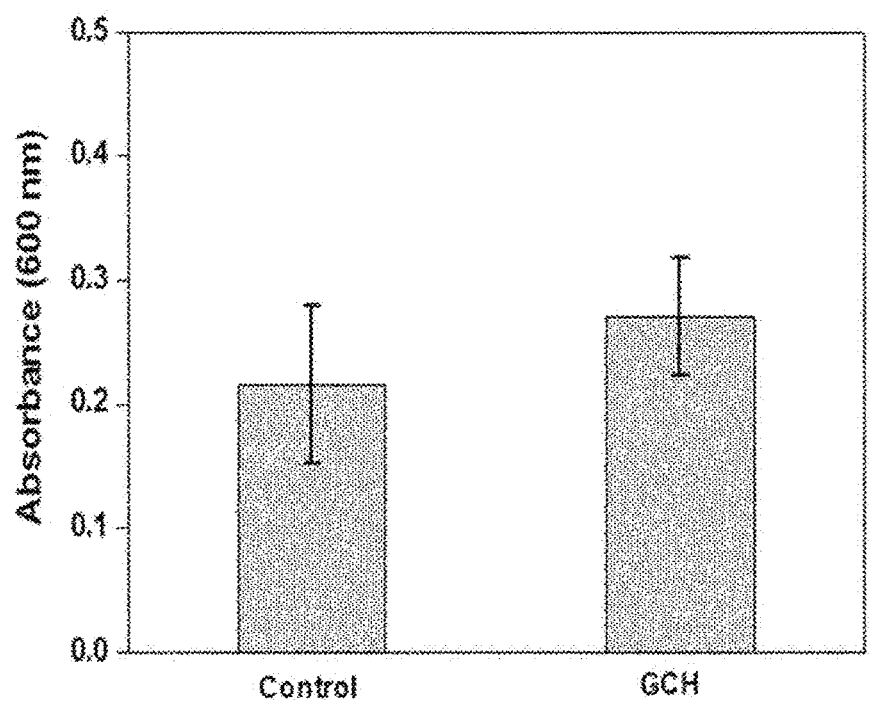
【Figure 3】
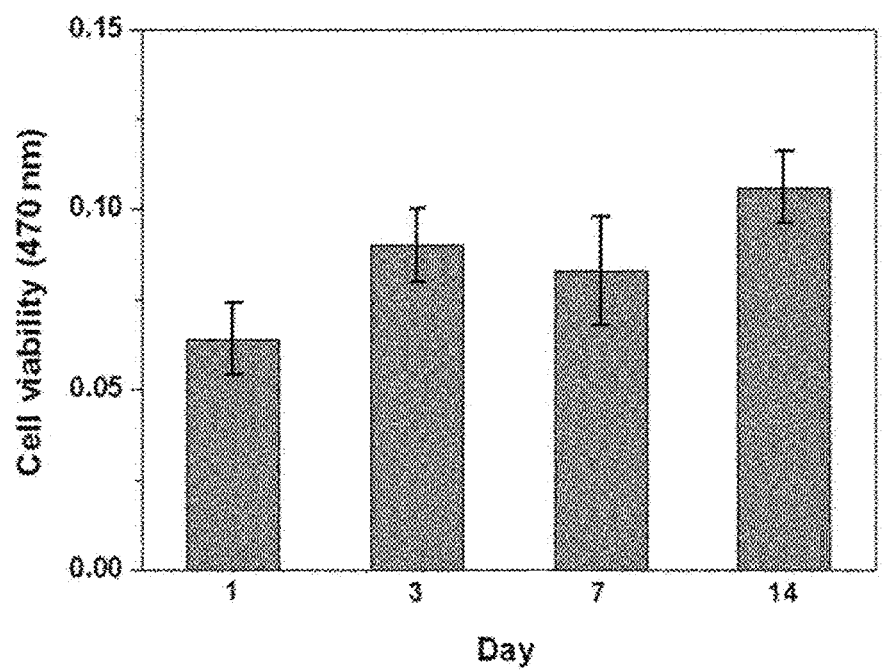

[Figure 4]
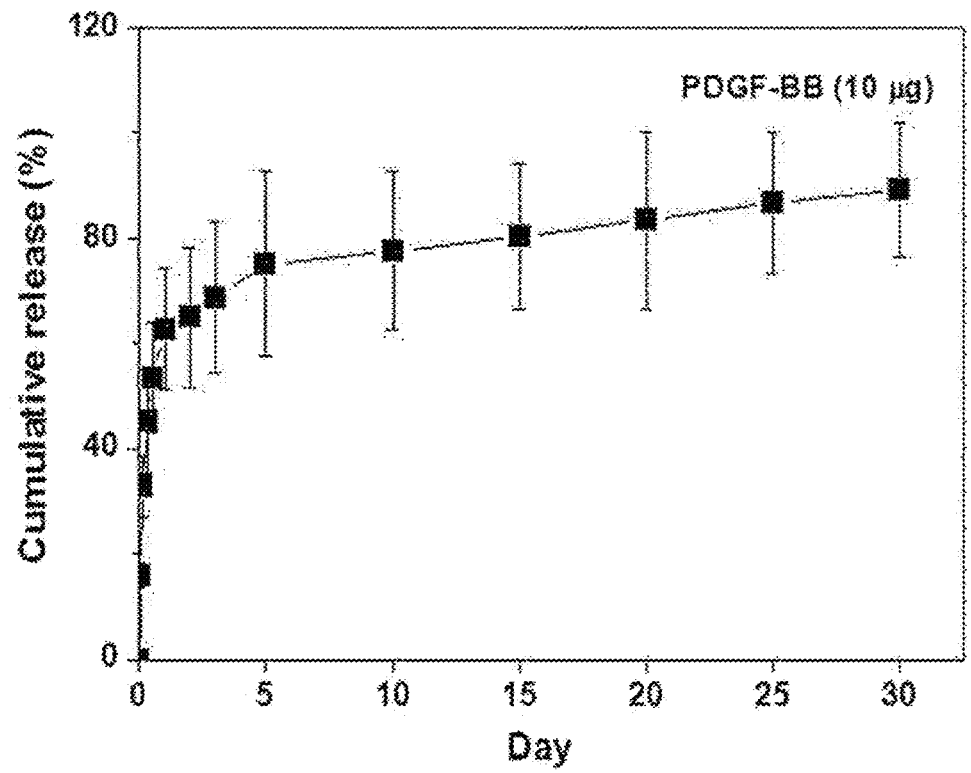

[Figure 5]
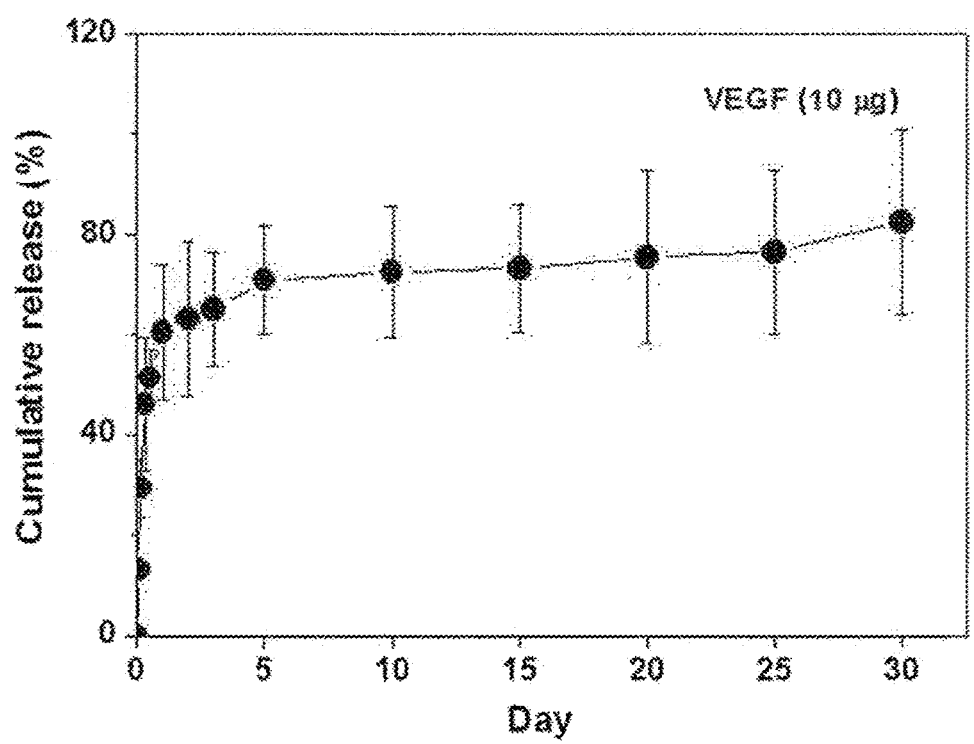

[Figure 6]
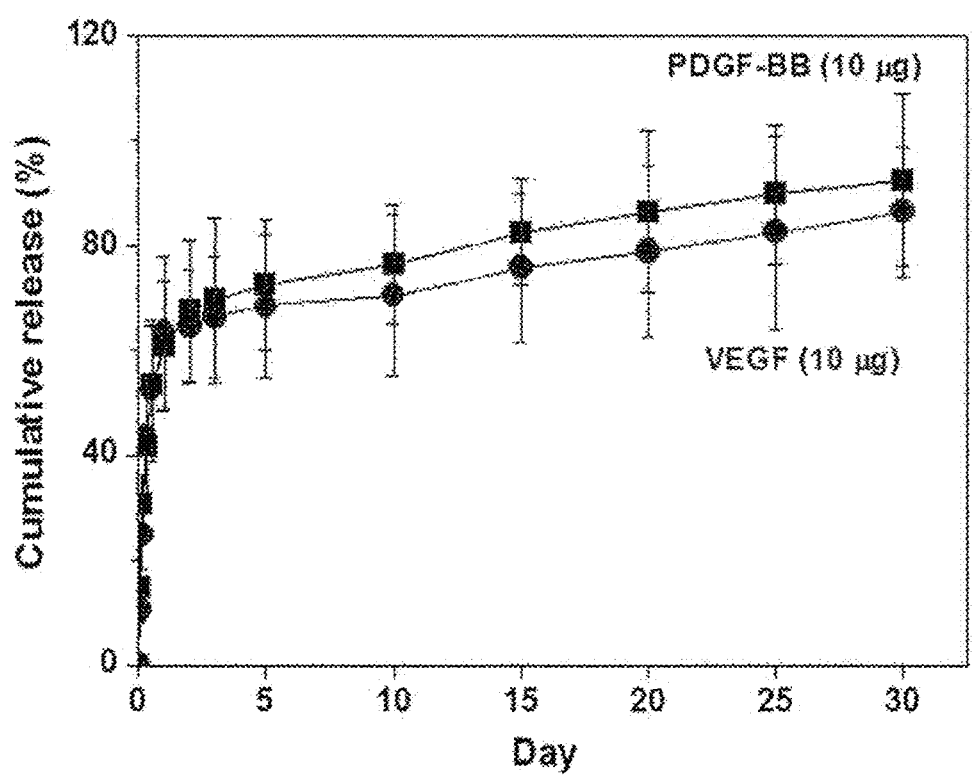

【Figure 7】
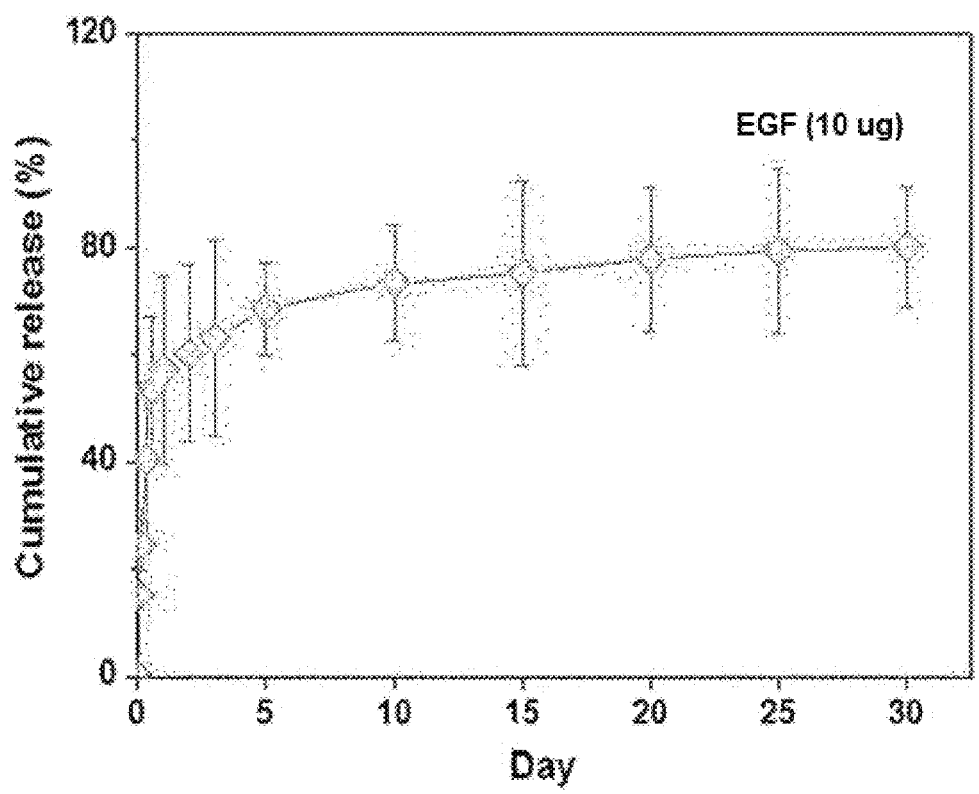

[Figure 8]
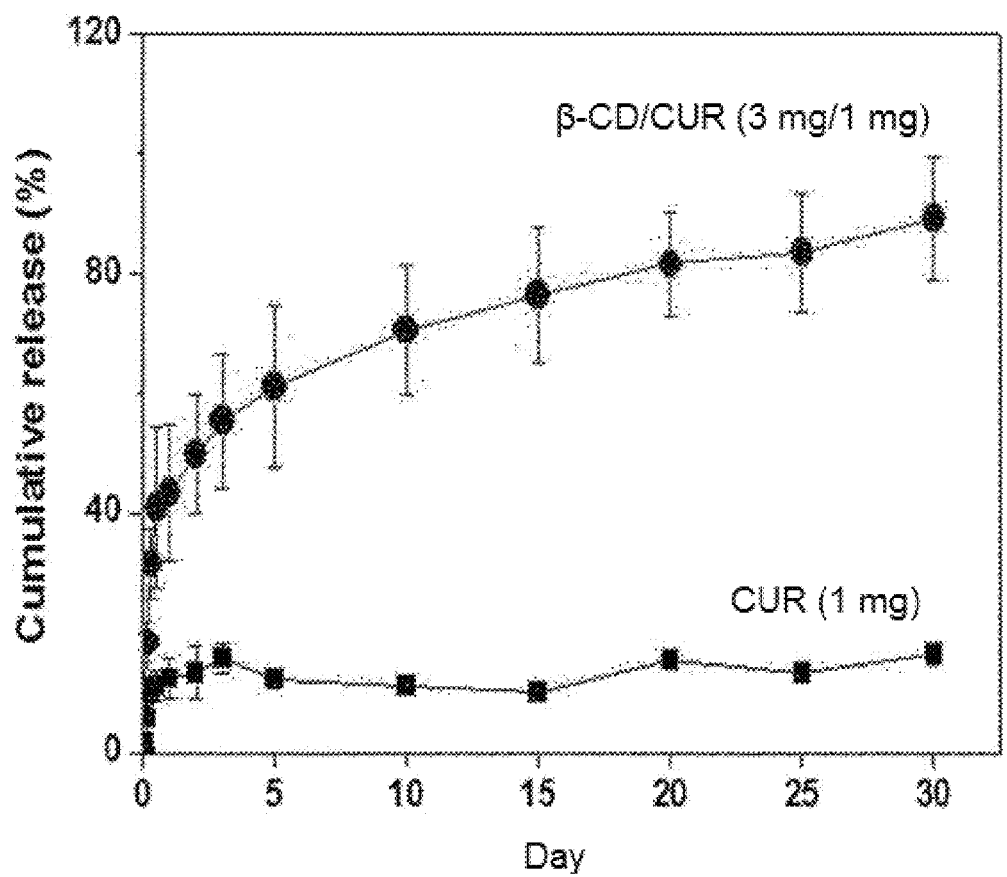

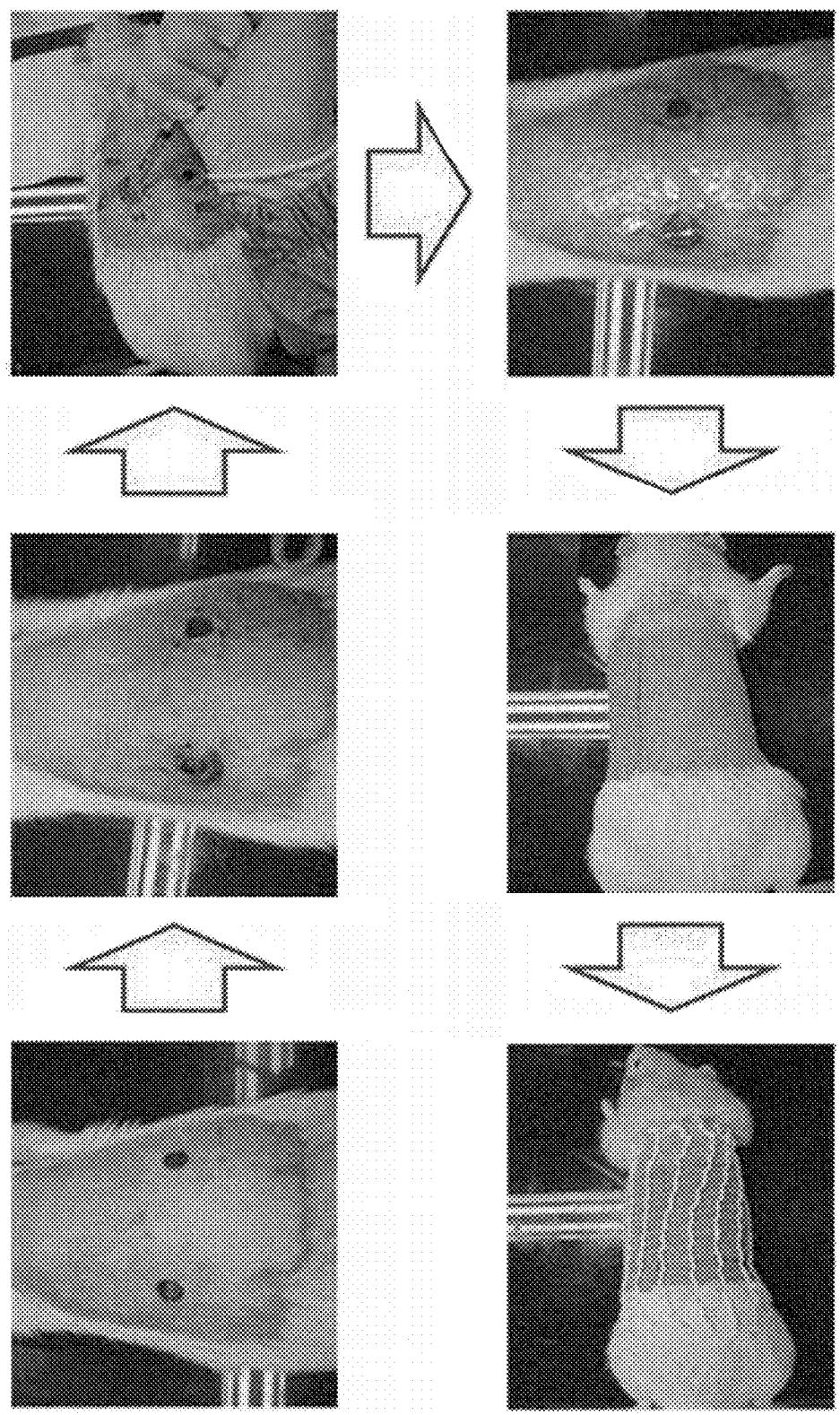
[Figure 9]

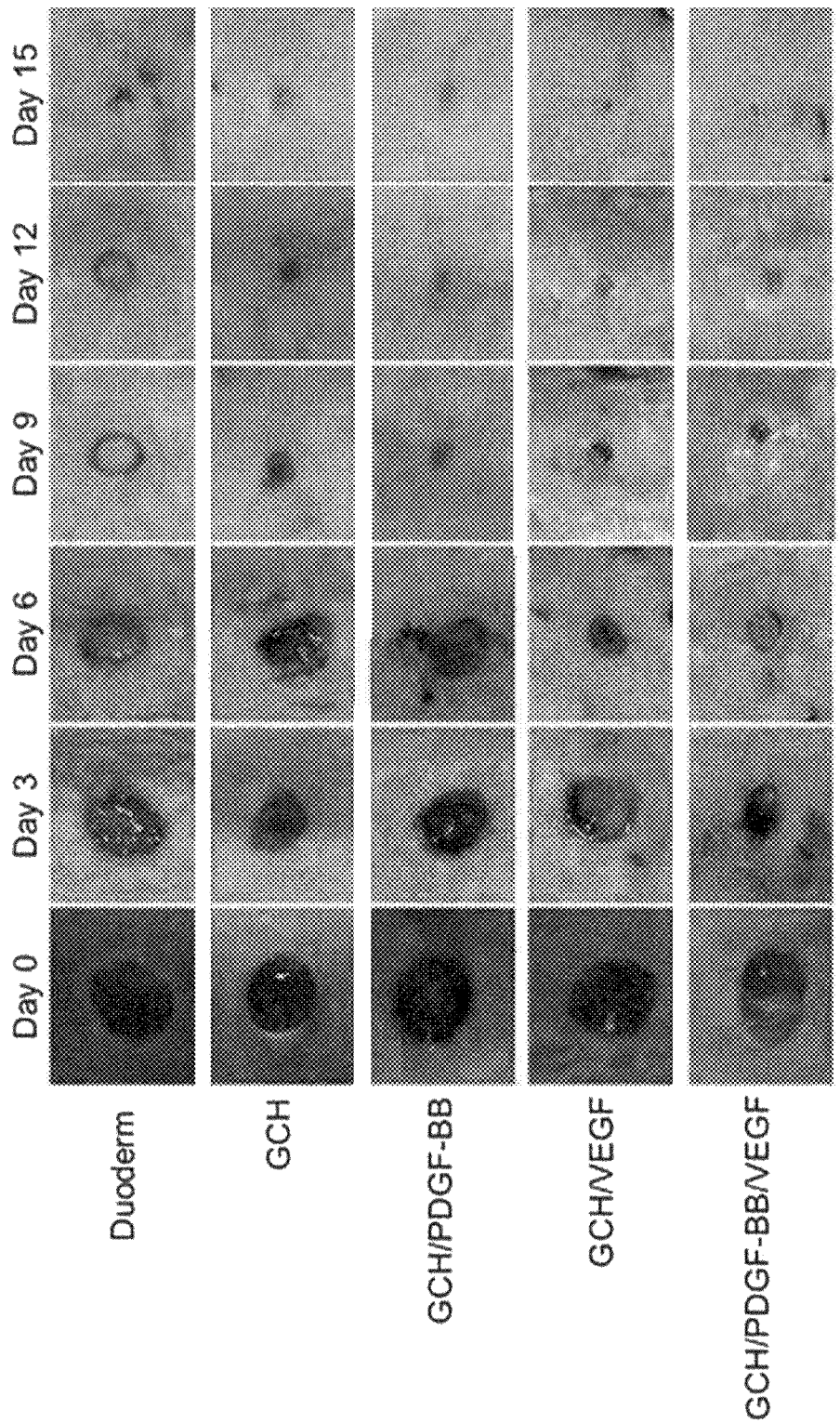
[Figure 10]

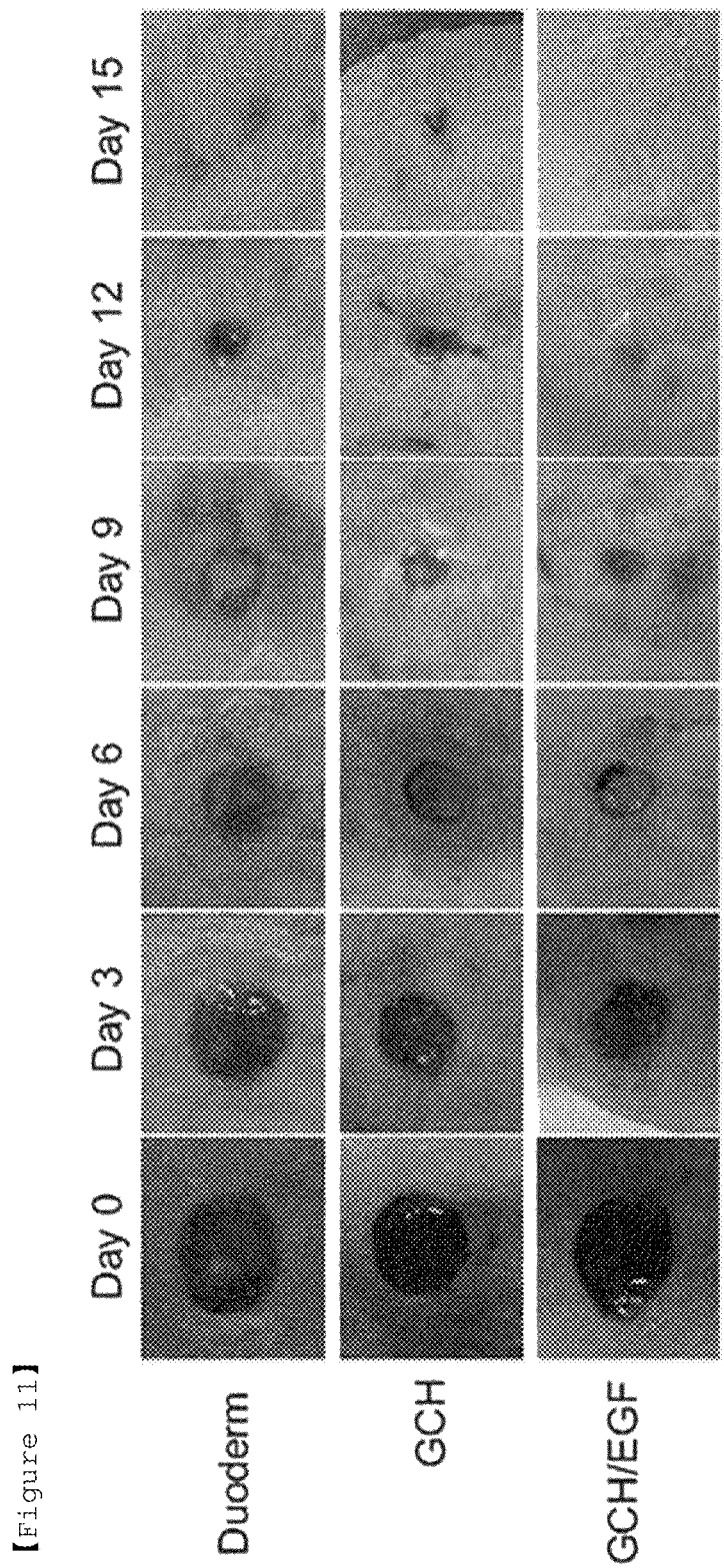
[Figure 11]

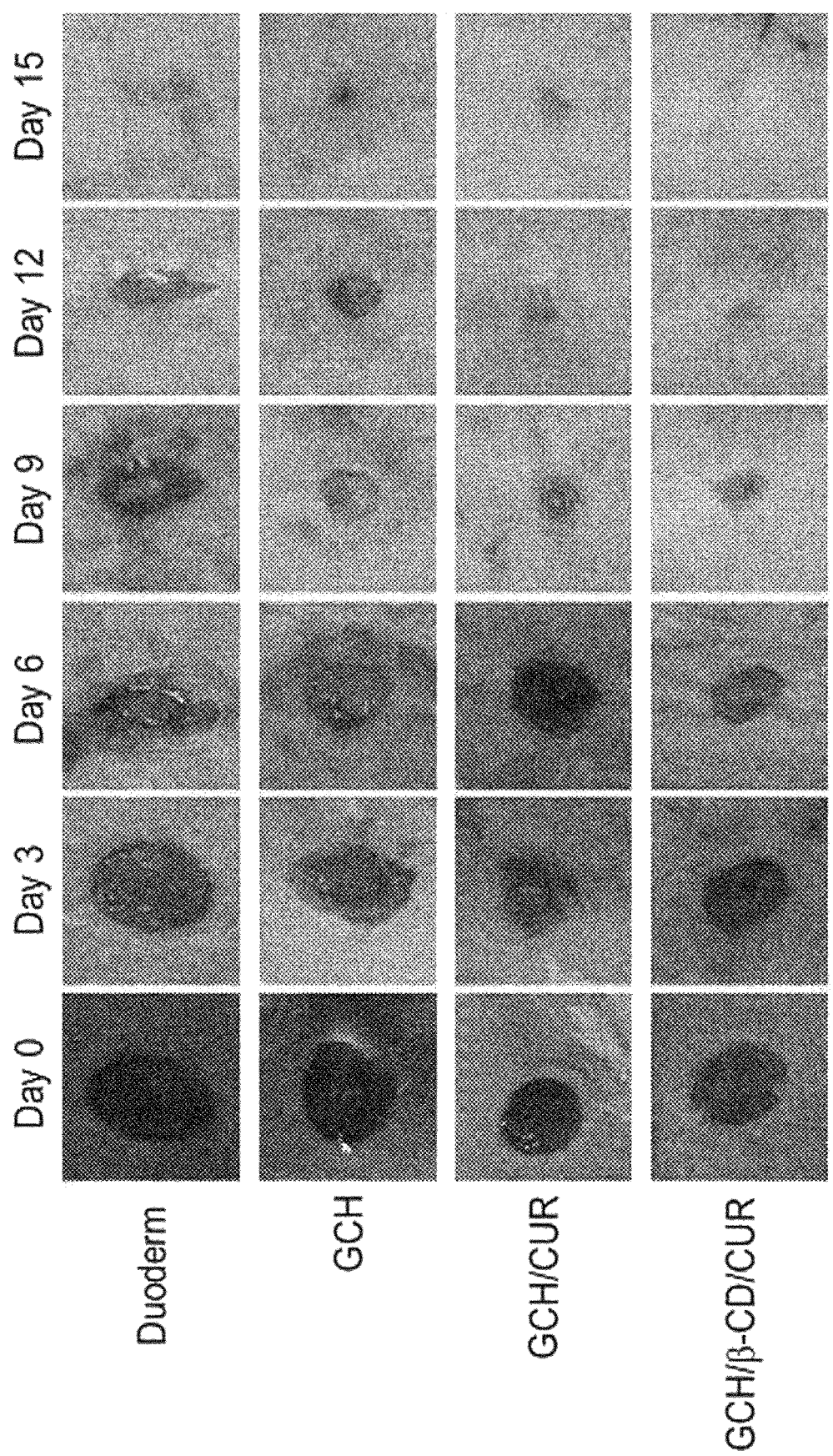
[Figure 12]

【Figure 13】
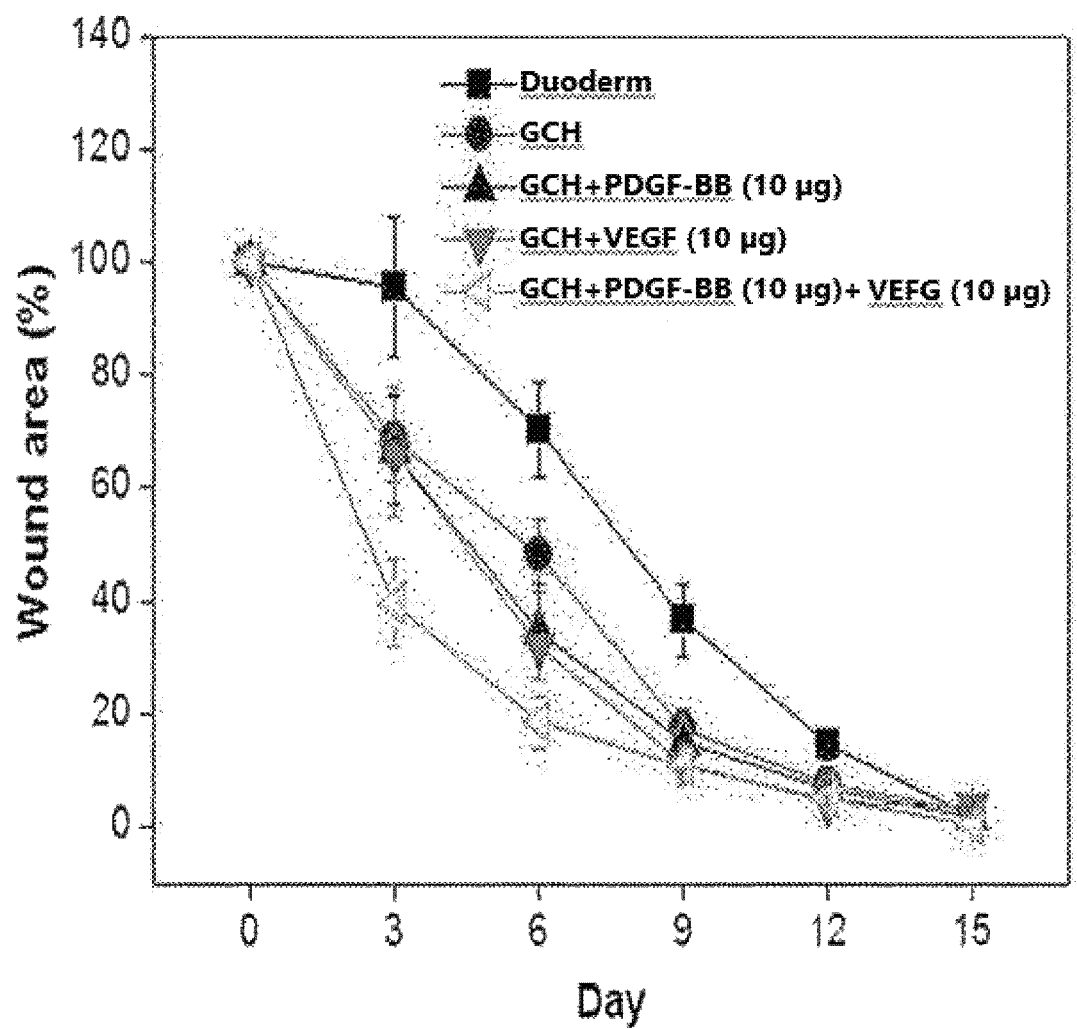

[Figure 14]
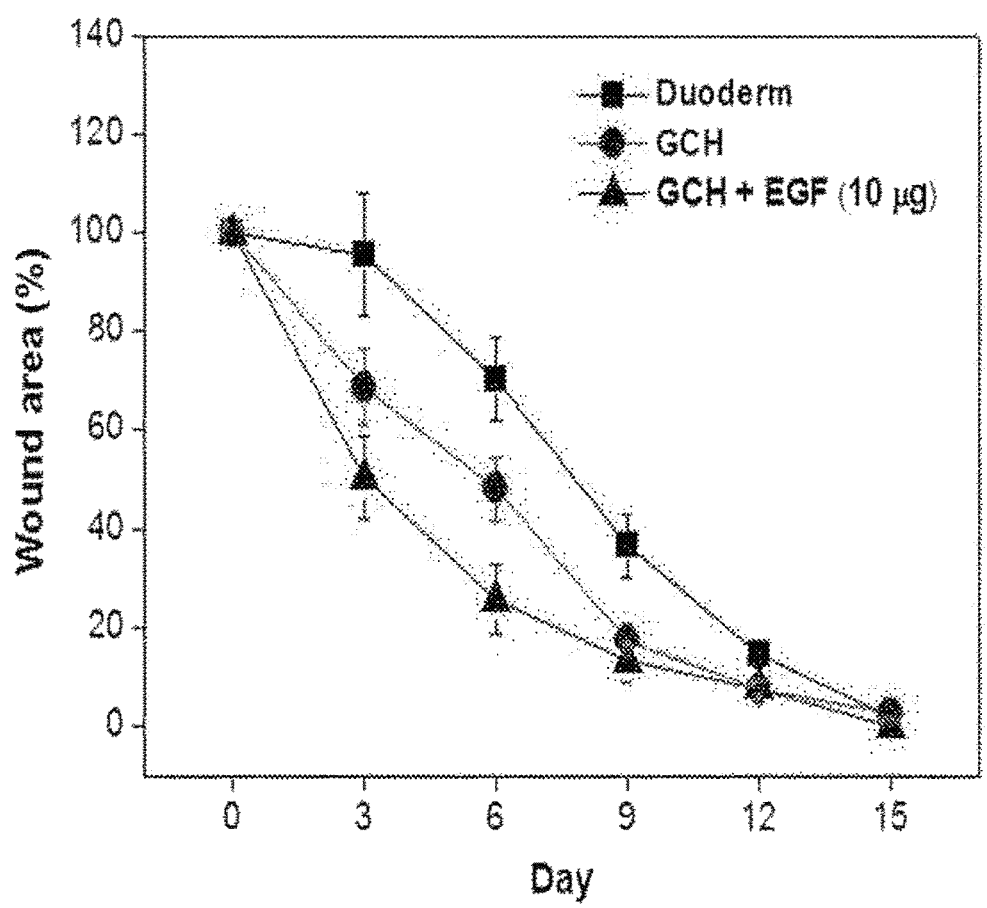

【Figure 15】
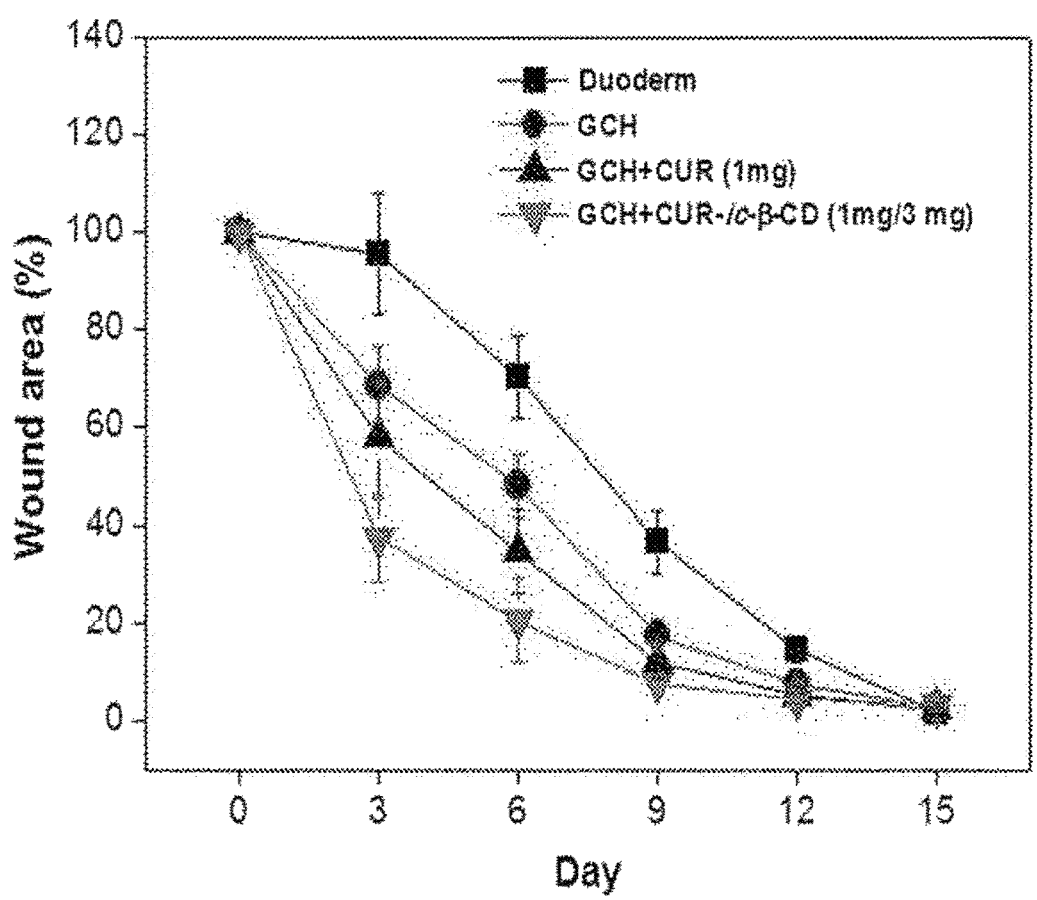

VISIBLE LIGHT-CURABLE WATER-SOLUBLE CHITOSAN DERIVATIVE, CHITOSAN HYDROGEL, AND PREPARATION METHOD THEREFOR

CROSS REFERENCE TO RELATED APPLICATIONS

This application is a continuation-in-part of application Ser. No. 16/323,634 filed Feb. 6, 2019, which is a National Stage of International Application No. PCT/KR2017/006393 filed Jun. 19, 2017, claiming priority based on Korean Patent Application No. 10-2016-0102602 filed Aug. 11, 2016, of which the entire contents are incorporated by reference herein.

TECHNICAL FIELD

The present invention relates to a visible light-curable glycol chitosan derivative, a glycol chitosan hydrogel, and a method for preparing the same and, more specifically, to a visible light-curable glycol chitosan derivative which is cured by light in the visible light range and has wound healing ability, a glycol chitosan hydrogel, and a method for preparing the same.

BACKGROUND ART

The development over the past two decades or so in wet dressings that cover wounds and maintain a wet environment surpasses the development over the last few hundred years or so. Clinical data on these wet dressings demonstrate the stability and effectiveness of the wet environment provided by the wet dressing in treating acute wounds and chronic wounds which are considered as being untreatable wounds.

Under the wet environment, regenerative epithelial cells are developed smoothly along the surface of the wound, but under dry environment, they cannot be developed along the surface of the wound and progress along the inside of the skin, a wet environment, while making way, thereby resulting in slow wound healing and ineffective wound healing. Also, in the dry environment, the substances involved in wound healing, such as polynuclear leukocytes, macrophages, proteolytic enzymes, and cell growth factors, contained in the exudates are discharged to the outside or do not play their role, but in the wet environment, they can perform their role smoothly and thus the wound healing is proceeded efficiently.

Ideal wet dressing should create a wet environment in the wound area and absorb the leachate from the wound area, and in particular, hydrogel serves as an ideal wet dressing. Methods of manufacturing the wet dressing include an existing freeze-thaw method, a chemical reaction method using a crosslinking agent such as boric acid, glutaraldehyde and formaldehyde, a radiation method by electron beam or g-ray and the like. The freeze-thaw method can ensure the stability of drugs such as antibiotics, but the chemical reaction method or the radiation method modifies the drug. Accordingly, the wet dressing is made by the freeze-thaw method generally. In addition, the existing freeze-thaw method is a method of preparing by repeating three times a process of raising the temperature of the aqueous solution containing several water-soluble polymers such as polyvinyl alcohol (PVA), chitosan and sodium alginate and drugs and dissolving and mixing them, and then freezing at −20° C. for 18 hours and thawing at room temperature for 6 hours, and thus has no stability problems in the case of heat-resistant drugs but can cause denaturation in the case of protein or peptide drugs or growth factors.

Meanwhile, chitosan is a type of polysaccharide that exists in nature, which is a compound obtained by deacetylating chitin contained in the shell of the shrimp, the bone of the squid, and the cell wall of microorganisms such as fungi and bacteria, and the chitosan has been used in various industries since the mid-1980s. The main use of chitosan in the past was mainly limited to a wastewater treatment field such as flocculants, heavy metal adsorbents, and dye wastewater purifiers and an agricultural field such as soil conditioners, pesticides, plant antivirals, and pesticides. However, as the advantages and various characteristics of chitosan have been revealed, the use of chitosan is expanding its scope to food and beverage applications, health hygiene application field, cosmetics applications, textile related applications and pharmaceutical applications. Particularly, since the 1990s, as chitosan has attracted attention as a usable material for medical materials, the use of chitosan in wound healing agents, artificial skin, coloring materials, blood coagulants, artificial kidney membranes, biodegradability surgical sutures, and antibiotic materials has been reported However, chitosan is a cationic polysaccharide in which glucose amine and N-acetyl glucose amines are bonded by β-1, 4 bond, which has an acetyl amino group in the molecule which can lead to very strong intermolecular hydrogen bonding. Therefore, since chitosan is not soluble in water and organic solvents, it has many difficulties in application to industry. The chitosan, which can be dissolved in water, is a chitosan or chitooligosaccharide with low molecular weight, but the chitosan has been reported to have higher efficacy as the molecular weight increases (Jung B. O. et al., *J. Chitin Chitosan*, 6(1), 12~17(2004)). In order to prepare such water-soluble chitosan having high molecular weight, U.S. Pat. No. 3,533,940 discloses that the chitosan which can be dissolved in an acidic aqueous solution such as acetic acid was prepared by deacetylating chitin, and thus the chitosan is commercially available. However, when applied to wet dressing formulations used in the human body, such as wound healing, serious skin irritation may be caused by residual acids.

To solve the problem of this chitosan, glycol chitosan, which are water-soluble chitosan derivatives prepared by introducing hydrophilic ethylene glycol group, shows water-solubility at neutral pH. This glycol chitosan is attracting attention as a bio-medical material because this exhibits biocompatibility, antibiosis, biodegradability, non-toxicity and non-immunogenicity.

PRIOR ART DOCUMENT (Patent Document 1) Korean Patent No. 0546793, "Foam dressing using chitosan and method of preparing the same."
(Non-Patent Document 1) Jung B. O. et al., J. Chitin Chitosan, 6(1), 12~17, 2004.

DISCLOSURE

Technical Problem

The inventors of the present invention have researched various methods for solving the problems in applying the above-mentioned chitosan to skin and optimizing it for a wet dressing, and as a result, have completed the present invention by introducing a functional group for visible light crosslinking instead of chemical crosslinking or UV crosslinking, using a glycol chitosan derivative to enhance biocompatibility.

Accordingly, it is an object of the present invention to provide a water-soluble glycol chitosan derivative that is photocured by visible light and a method for preparing the same.

In addition, it is another object of the present invention to provide a glycol chitosan hydrogel comprising the glycol chitosan derivative and a method for preparing the glycol chitosan hydrogel.

In addition, it is still another object of the present invention to provide a wet dressing for healing wounds comprising the glycol chitosan hydrogel.

Technical Solution

In order to achieve the above objects, the present invention provides a visible light-curable glycol chitosan derivative represented by the following Formula 1 and a method for preparing the same.

DESCRIPTION OF DRAWINGS

FIG. 1a is a method for preparing the visible light-curable glycol chitosan derivative according to the present invention, and FIG. 1b is a $^1$H NMR analysis ($D_2O$) data of the visible light-curable glycol chitosan derivative.

FIG. 2 is a graph of cytotoxicity of the glycol chitosan hydrogel by microbial culture according to the present invention.

FIG. 3 is a graph of the L-929 cell viability by three-dimensional culture of the glycol chitosan hydrogel according to the present invention.

FIG. 4 is a graph showing release behavior according to a function of time from the glycol chitosan hydrogel comprising PDGF-BB according to the present invention.

FIG. 5 is a graph showing release behavior according to a function of time from the glycol chitosan hydrogel comprising VEGF according to the present invention.

FIG. 6 is a graph showing release behavior according to a function of time from the glycol chitosan hydrogel comprising PDGF-BB/VEGF according to the present invention.

[Formula 1]

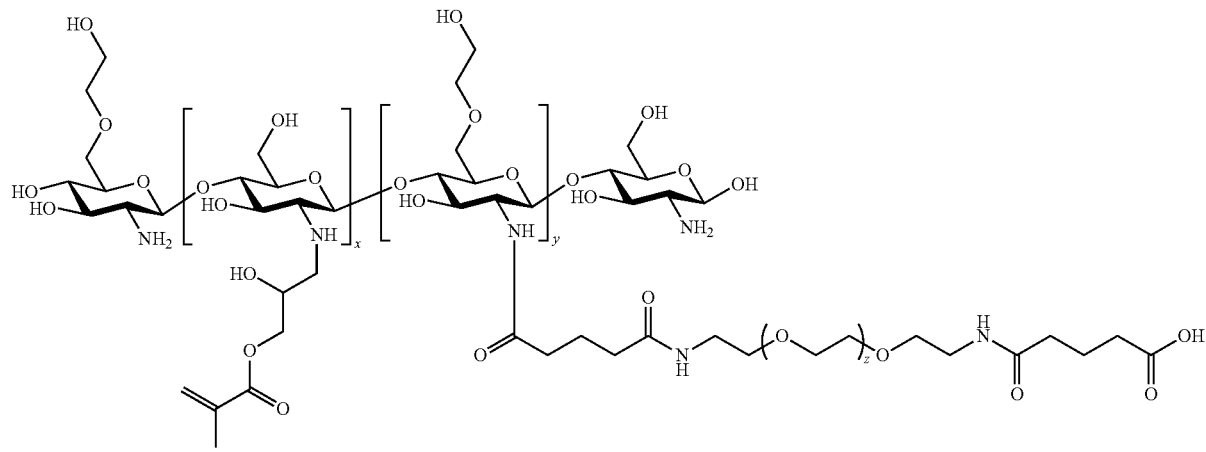

wherein x+y is an integer of 20 to 100, and z is an integer of 20 to 115.

In addition, the present invention provides a glycol chitosan hydrogel comprising the visible light-curable chitosan derivative and a method of preparing the glycol chitosan hydrogel.

In addition, the present invention provides a wet dressing material for healing wounds comprising the glycol chitosan hydrogel.

Advantageous Effects

A hydrogel obtained by cross-linking the visible light-curable glycol chitosan derivative according to the present invention by visible light is effective for healing wounds by itself, and also the hydrogel obtained by cross-linking along with growth factors alone or in combination of two or more is excellent in wound healing effect. Also, a glycol chitosan hydrogel that can prevent the denaturation of contained drugs and growth factors due to the cross-linking by visible light and is optimized for the dosage form of wet dressing can be prepared.

FIG. 7 is a graph showing release behavior according to a function of time from the glycol chitosan hydrogel comprising EGF according to the present invention.

FIG. 8 is a graph showing release behavior according to a function of time from the glycol chitosan hydrogel comprising CUR and beta-cyclodextrin (beta-CD)/CUR according to the present invention.

FIG. 9 is an explanatory diagram showing a series of processes for applying a sample to the back of a mouse from which the skin tissue has been removed according to the present invention.

FIG. 10 is a photograph showing a wound healing effect using the glycol chitosan hydrogel comprising Duoderm®, glycol chitosan hydrogel (GCH) and PDGF-BB, VEGF, PDGF-BB/VEGF.

FIG. 11 is a photograph showing a wound healing effect using the glycol chitosan hydrogel comprising Duoderm®, glycol chitosan hydrogel (GCH) and EGF.

FIG. 12 is a photograph showing a wound healing effect using the glycol chitosan hydrogel comprising Duoderm®, glycol chitosan hydrogel (GCH) and CUR and beta-CD/CUR.

FIG. 13 is a graph showing the area in % of wound area healed according to the passage of time by the glycol chitosan hydrogel comprising Duoderm®, glycol chitosan hydrogel (GCH) and PDGF-BB, VEGF and PDGF-BB/VEGF.

FIG. 14 is a graph showing the area in % of wound area healed according to the passage of time by the glycol chitosan hydrogel comprising Duoderm®, glycol chitosan hydrogel (GCH) and EGF.

FIG. 15 is a graph showing the area in % of wound area healed according to the passage of time by the glycol chitosan hydrogel comprising Duoderm®, glycol chitosan hydrogel (GCH) and CUR and beta-CD/CUR.

BEST MODE

The present invention provides a glycol chitosan derivative represented by the following Formula 1. The glycol chitosan derivative according to the present invention can form a hydrogel by being cured by visible light:

[Formula 1]

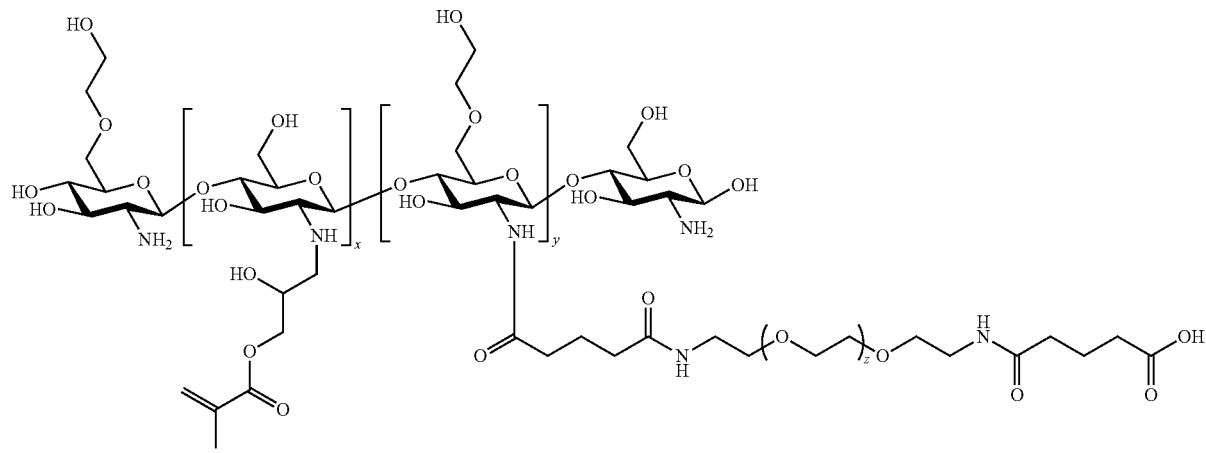

wherein x+y is an integer of 20 to 100, and z is an integer of 20 to 115.

The glycol chitosan derivative of the Formula 1 may be prepared by reacting the glycol chitosan (GC) represented by Formula 2 sequentially with 1) glycidyl methacrylate (GM) and 2) polyethylene glycol-bis carboxylic acid according to the following Reaction Scheme 1:

[Reaction Scheme 1]

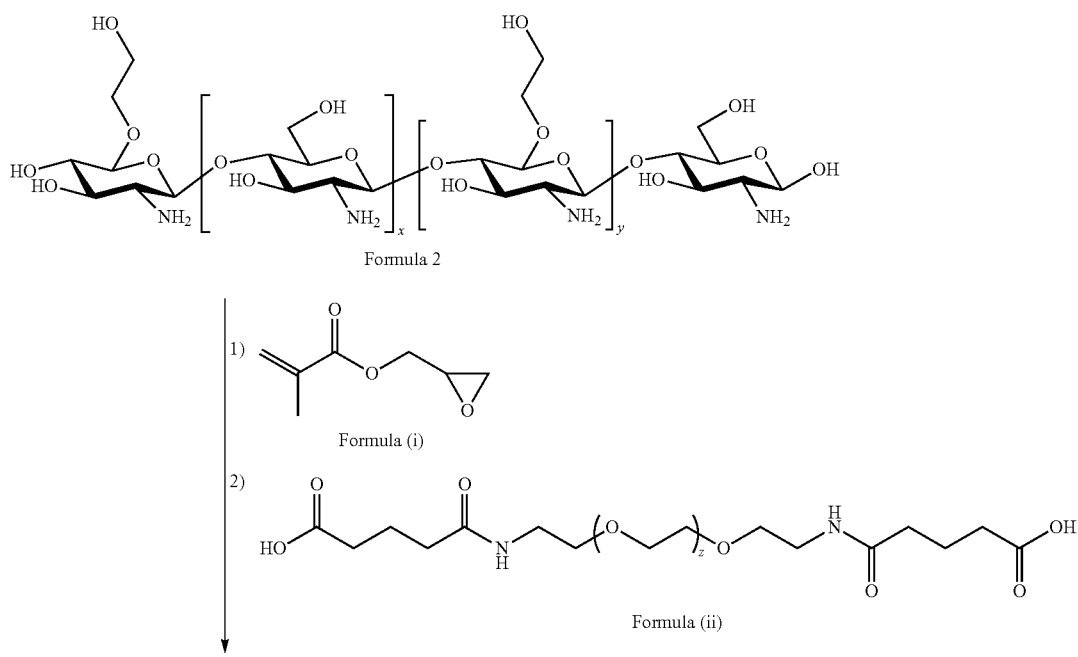

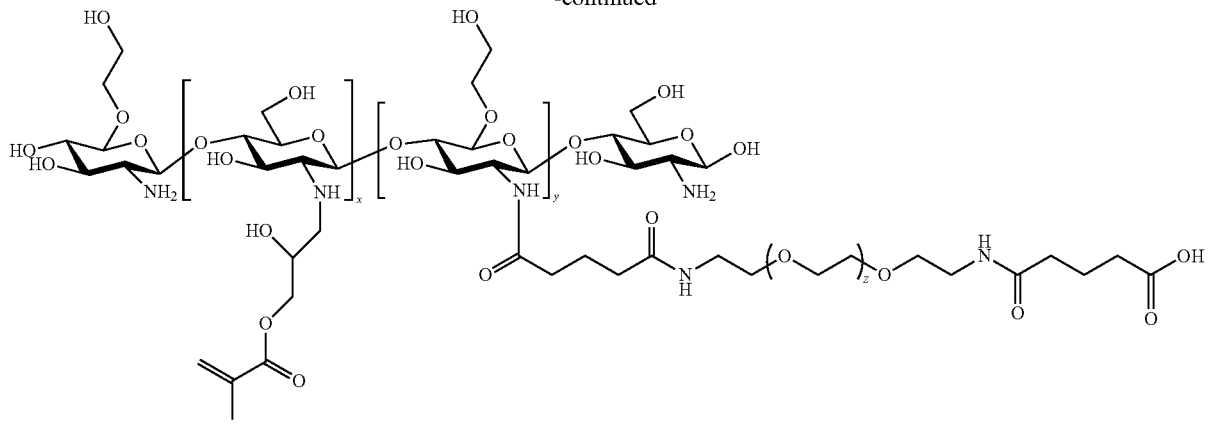

Formula 1 wherein x, y and z are as defined in the above Formula 1.

The glycidyl methacrylate (GM) of component 1) acts as a functional group for photocuring by visible light, and the polyethylene glycol-bis carboxylic acid of component 2) acts as a functional group to modify to water solubility in order to improve biocompatibility. As a result, the glycidyl methacrylate (GM) and PEG-bis carboxylic acid are chemically bonded by the amide bond formed by condensation reaction with the amine group of the glycol chitosan (GC).

The glycol chitosan derivative represented by the above Formula 1 can form a glycol chitosan hydrogel by cross-linking by visible light at the range of 435-480 nm while using riboflavin as a photo-initiator. At this time, the glycol chitosan derivative can form a composition for healing wounds which can be photocured alone or along with growth factors or drugs.

At this time, the growth factors which can be applied may be selected, for example, from platelet-derived growth factor (PDGF), vascular endothelial growth factor (VEGF), epidermal growth factor (EGF), fibroblast growth factor (FGF), hepatocyte growth factor (HGF), trans-forming growth factor (TGF), insulin-like growth factor (IGF), placental growth factor (PIGF), nerve growth factor (NGF), bone-derived growth factor (BDF), brain-derived neutrophic factor (BDNF), colony stimulation factor (CSF) and the combination thereof, and the drug can be a water-soluble drug that can be obtained by hydrophilization of curcumin, which is a poorly soluble drug, with beta-cyclodextrin (beta-CD).

The composition containing the glycol chitosan hydrogel has a wound healing effect and can be formed into various shapes before the curing is induced by visible light. Therefore, if the composition is subjected to visible light irradiation after molding according to its purpose and use, the composition may be formulated into a film form, a form including a curved face, or the like depending on various living body parts.

The composition for healing wounds comprising the glycol chitosan hydrogel of the present invention may be formulated to include a pharmaceutical carrier. The compositions may be applied to the skin or wound in the form of cream, spray, foam, gel or in any other dosage form.

In addition, the composition for healing wounds comprising the glycol chitosan hydrogel further may include at least one component selected from collagen, gelatin, xanthan gum, carrageenan, agar, alginic acid or a salt thereof, hyaluronic acid or a salt thereof, pectin, starch, polyacrylic acid or a salt thereof, polyvinyl alcohol, polyvinyl pyrrolidone, polyethylene oxide, methyl vinyl ether maleic anhydride copolymer, isobutylene maleic anhydride copolymer, methacrylic acid butyl acrylate copolymer, methoxy ethylene maleic anhydride copolymer, sodium carboxymethylcellulose, soluble starch and carboxymethyl starch.

In particular, the composition for healing wounds comprising the glycol chitosan hydrogel may preferably be formulated into a wet dressing material for healing wounds comprising a therapeutically effective amount by impregnating into or covalently attaching to a covering or dressing material. The dressing material may be any material used in the art, including bandages, gauzes, sterile packaging materials, hydrogel, hydrocolloids or similar materials. In the present invention, the therapeutically effective amount of the chitosan derivative is an amount necessary for promoting healthy skin development or wound healing. The therapeutically effective amount depends not only on the route of administration but also on the nature of the symptoms to be treated, and the age and symptom of the patient, which may be considered by the physician or clinician.

The pad for laminating the glycol chitosan hydrogel to the support may be prepared by laminating a polyurethane film, a polyethylene phthalate film, or a polyethylene film with any one selected from natural and chemical fibers such as nonwoven fabric, fibers, cotton, and rayon or the combination of two or more thereof.

For example, the wet dressing material for healing wounds according to the present invention can be provided as a chitosan hydrogel patch for treating wounds in a transparent or semi-transparent state, which is obtained by laminating an adhesive polyurethane film having a cutting support laminated thereon and having a function of preventing moisture release from the skin and moisture penetration from the outside with a hydrogel pad containing hydrogel laminated on a support wherein the hydrogel is composed of glycol chitosan hydrogel according to the present invention, polyacrylic acid or its salt, water-soluble polymer such as sodium carboxymethylcellulose, polyol such as glycerin, cross-linking agent and the like, and which has a structure covered with a release film or release paper so that the hydrogel layer directly contacting the wound site can be protected from external contamination.

Since the glycol chitosan derivative according to the present invention has a visible light curing property which is cured by visible light irradiation and thus has a property of inhibiting cell adhesion, the glycol chitosan derivative can be effectively used as an anti-adhesion agent and can be developed as a wound healing promoting agent because it exhibits wound healing promoting effects even without wound healing drugs. Also, according to the present invention, it is possible to prevent denaturation of growth factors or drugs contained because it is not a conventional chemical crosslinking or crosslinking by UV.

Hereinafter, preferred embodiments of the present invention will be described in detail with reference to the accompanying drawings. These drawings may be embodied in various different forms as an embodiment for explaining the present invention, and are not limited thereto.

Example 1: Synthesis of Visible Light Curable Glycol Chitosan Derivative

Glycol chitosan ($1.8 \times 10^{-6}$ mol, 1 g) and glycidyl methacrylate (0.0035 mol, 0.5 g) were dissolved in an aqueous NaOH solution (pH 9, 100 mL), reacted at room temperature for 3 days, and dialyzed for 3 days (MWCO 2,000), and then lyophilized (GC/GM). GC/GM ($8.8 \times 10^{-7}$ mol, 0.5 g), polyethylene glycol bicaboxylic acid$_{1k}$ ($8.8 \times 10^{-4}$ mol, 0.88 g) and 4-(4,6-Dimethoxy-1,3,5-triazin-2-yl)-4-methylmorpholinium chloride (DMT-MM) ($8.8 \times 10^{-4}$ mol, 0.25 g) were added, and reacted at room temperature for 3 days, dialyzed for 3 days (MWCO 10,000), lyophilized and analyzed by $^1$H NMR on $D_{2O}$. The results are shown in FIG. 1, and it was confirmed that PEG-biscarboxylic acid (MW 1 k) for improving biocompatibility and glycidyl methmetacrylate (GM) for photocuring by visible light range were chemically bonded by amide bond by condensation to the amine group of glycol chitosan (GC).

Example 2: Formation of Glycol Chitosan Hydrogel

In order to sterilize the glycol chitosan hydrogel, the visible light-curable glycol chitosan derivative prepared in Example 1 was filtered through a 0.22 μm filter, and then 1 ml of mixed solution of filtered light-curable glycol chitosan derivative (2 wt. %, 900 μl) and riboflavin (120 μM, 100 μl) was placed in a 15 ml tube, and then irradiated with a visible light irradiator (460 nm) for 40 seconds to prepare a glycol chitosan hydrogel (GCH).

Experimental Example 1: Evaluation of In Vitro Cytotoxicity of Glycol Chitosan Hydrogel 5 ml of LB broth was added to the glycol chitosan hydrogel (GCH) prepared in Example 2, wherein the LB broth was used without ampicillin added in order to see that the microorganisms were cultured. 5 ml of LB broth without glycol chitosan hydrogel (GCH) was used as a control. Two samples were placed in an incubator and incubated for 48 hours. Absorbance was measured at 600 nm using a spectrophotometer.

As shown in FIG. 2, it was confirmed that there is no significant cytotoxicity of the glycol chitosan hydrogel as compared to the control.

Experimental Example 2: Analysis of Cell Viability

L-929 cells ($6.25 \times 10^{-5}$ cells/m L) were mixed with glycol chitosan derivative solution, and then 60 μl of aliquot were added to 96-well plates respectively to confirm cell viability for 1, 3, 7 and 14 days. Each well was irradiated with a visible light irradiator for 40 sec, thereby inducing gelation, and then 100 μl of media was added to each well. The media was a mixture of RPMI 1640 89%, FBS 10%, and Penicillin/Streptomycin 1%. After 1, 3, 7, and 14 days, CCK-8 (6 μl) reagent was added and incubated for 2 hours and then measured for absorbance at 470 nm using ELISA.

As shown in FIG. 3, it can be seen that the cell viability of the glycol chitosan prepared was increased with time. Of course, the average cell viability on the 7th day was slightly lower than that on the 3rd day, but it was judged that it is difficult to judge that the cell viability was lowered because it was within the error range. From these results, the glycol chitosan hydrogel is considered to be suitable for the development of wet dressing material for healing wounds.

Experimental Example 3: In Vitro Release Test of PDGF-BB, VEGF, PDGF-BB/VEGF and EGF Four samples prepared by adding 10 μl of each of PDGF-BB, VEGF, PDGF-BBNEGF and EGF to glycol chitosan hydrogel (initial weight of 10 mg) prepared in Example 2 were placed in a 100 kDa dialysis membrane and then immersed in a tube containing 5 ml of 0.1 M PBS (pH 7.4). Each sample of 1 ml of PBS was collected for 30 days at a designated time (0 h, 1 h, 3 h, 7 h, 12 h, 1 d, 2 d, 3 d, 5 d, 10 d, 15 d, 20 d, 25 d, 30 d) and filled with 1 ml of fresh PBS, respectively. Release behavior was analyzed using ELISA according to the manufacturer's instructions.

FIGS. 4 to 7 are graphs showing release behavior from glycol chitosan hydrogel containing a growth factor according to a function of time wherein FIG. 4 is a graph of the release behavior of PDGF-BB, FIG. 5 is a graph of the release behavior of VEGF, FIG. 6 is a graph of the release behavior of PDGF-BBNEGF, and FIG. 7 is a graph of the release behavior of EGF. In the case of PDGF-BB and VEGF, the initial burst from the hydrogel containing each growth factor occurs in the range of 50 to 60% for 1 day, and the drug is released continuously for 30 days. As a result of confirming the release behavior by mixing two growth factors of PDGF-BB and VEGF, the same behavior as each drug release shown in FIG. 4 and FIG. 5 was shown. In the case of FIG. 7, the release behavior of EGF is similar to the release behavior graphs of FIG. 4 to FIG. 6.

Experimental Example 4: In Vitro Release Test of Curcumin (CUR)

Glycol chitosan hydrogel (initial weight of 10 mg) containing 1 mg of CUR and 3 mg/l mg of beta-CD/CUR were placed in a 15 ml tube containing 3 ml of PBS (pH 7.4), and then the release behavior was examined in an incubator at 37° C. and 100 rpm. Each sample of 1 ml of PBS was collected for 30 days at a designated time (0 h, 1 h, 3 h, 7 h, 12 h, 1 d, 2 d, 3 d, 5 d, 10 d, 15 d, 20 d, 25 d, 30 d) and filled with 1 ml of fresh PBS respectively. Release behavior was determined by measuring the absorbance at $\lambda_{max}$=491.2 nm using UV-vis spectrophotometer.

FIG. 8 is a graph showing release behavior according to a function of time from the glycol chitosan hydrogel comprising CUR and beta-CD/CUR. As shown in FIG. 8, it was confirmed that the poorly soluble CUR is not released smoothly from the glycol chitosan hydrogel. However, it was confirmed that in the case of beta-CD/CUR, since CUR forms inclusion complex with beta-CD to become water-soluble, the release behavior is proceeded relatively smoothly. The reason for the sustained release behavior of growth factor and beta-CD/CUR is thought to be that the glycol chitosan hydrogel helps to control the release.

Experimental Example 5: Preliminary Animal Experiment Using Mouse

In order to confirm the therapeutic efficacy of wounded skin by the glycol chitosan hydrogel containing PDGF-BB, VEGF, PDGF-BB/VEGF, EGF, CUR and beta-CD/CUR, animal experiments were performed using Balb C mice (male, average weight: 20 g). Animal experiments were approved by the Institutional Animal Care and Use Committee (IACUC) of Kangdong Kyunghee University Hospital (KHNMC AP 2015-008). Mice were anesthetized by administering a mixed solution of Zoletil and Rompun, and then the dorsal hairs of the mice were removed using an electric shaver. The skin tissue was detached from the shaved surface using a punch having a diameter of 5 mm, and then applied once every three days using the prepared sample. The skin tissue regeneration was confirmed by photographs every 3 days for a total of 15 days. On day 15, mice were sacrificed and regenerated skin tissues were removed and blocks were prepared for tissue staining and immunochemical staining. FIG. 9 is a photograph showing a portion of the skin where the skin tissue is removed so as to have a diameter of 5 mm on the back region of the mouse.

FIG. 10 is data that visually display the degree of healing over time after applying the formulations from the glycol chitosan hydrogel (GCH) alone prepared in the Example 2 and from the glycol chitosan hydrogel (GCH) containing PDGF-BB, VEGF, and PDGF-BB/VEGF to the wound site. The control group was treated with Duoderm®, a commercially available wound healing ointment. It was confirmed that when treated with the glycol chitosan hydrogel (GCH) alone, the wound was healed more quickly compared to Duoderm®, and when treated with the glycol chitosan hydrogel (GCH) containing PDGF-BB, VEGF, and PDGF-BB/VEGF, the wound was healed more quickly compared to the glycol chitosan hydrogel (GCH) alone. In particular, it was visually confirmed that in the case of PDGF-BB/VEGF mixed with two growth factors, the wound healing effect is promoted more than when using growth factor alone.

FIG. 11 is a data visually showing the degree of healing over time after application of the glycol chitosan hydrogel containing EGF to a wound site. It was confirmed that in the case of the glycol chitosan hydrogel containing EGF, the skin at the wound area was healed more quickly than when using Duoderm® or the glycol chitosan hydrogel (GCH) alone, and the wound area was completely recovered on the 15th day.

FIG. 12 is a data visually showing the degree of healing over time after application of the glycol chitosan hydrogel (GCH) containing CUR (curcumin) and beta-CD/CUR to a wound site. It was confirmed that in the case of the glycol chitosan hydrogel containing CUR and beta-CD/CUR, the skin at the wound area was healed more quickly than when using Duoderm® or the glycol chitosan hydrogel (GCH) alone. In particular, it was confirmed that in the case of the hydrogel containing beta-CD/CUR, wound healing was promoted more than when using the hydrogel containing CUR. This is probably due to improved bioavailability of CUR by water-solubilizing the poorly soluble CUR using beta-CD.

FIGS. 13 to 15 are graphs showing the area in % of the healed wound site over time obtained by using FIGS. 10 to 12 described above. Referring to FIG. 13, it can be seen that in the case of the glycol chitosan hydrogel (GCH) containing a growth factor, the wound healing effect is faster than when using Duoderm® and the glycol chitosan hydrogel (GCH). In addition, it was confirmed that it is most effective to heal wounds using the glycol chitosan hydrogel (GCH) containing the mixture of PDGF-BB and VEGF. In FIG. 14, it was confirmed that the wound healing by using the glycol chitosan hydrogel (GCH) containing growth factor EGF is more effective than the wound healing obtained by using Duoderm® and the glycol chitosan hydrogel (GCH) alone. In FIG. 15, it was confirmed that the wound healing obtained by using the glycol chitosan hydrogel (GCH) containing CUR is more effective than the wound healing obtained by using Duoderm® and the glycol chitosan hydrogel (GCH) alone, and in particular, it was judged that improving the water solubility of CUR helps to heal wounds. These results are considered to be the result of increased bioavailability obtained by improving the water solubility of CUR.

What is claimed is:
1. A visible light-curable glycol chitosan of the following Formula 1:

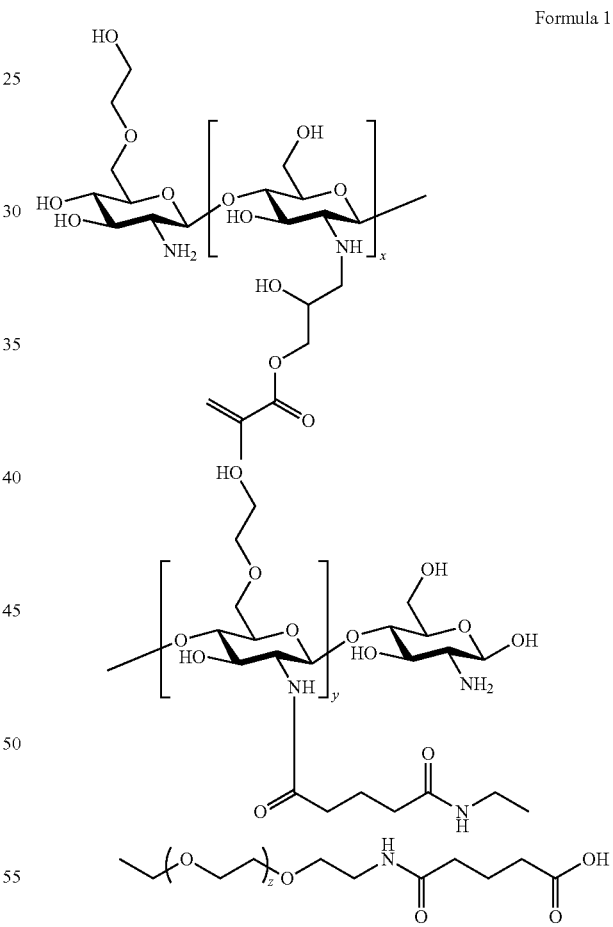

Formula 1 wherein x+y is an integer of 20 to 100 and z is an integer of 20 to 115; and wherein both x and y are greater than zero.

2. A glycol chitosan hydrogel obtained by crosslinking the visible light-curable glycol chitosan of claim 1.

3. A composition comprising the glycol chitosan hydrogel according to claim 2 and a growth factor.

4. The composition according to claim 3, wherein the growth factor is selected from the group consisting of platelet-derived growth factor (PDGF), vascular endothelial growth factor (VEGF), epidermal growth factor (EGF), fibroblast growth factor (FGF), hepatocyte growth factor (HGF), trans-forming growth factor (TGF), insulin-like growth factor (IGF), placental growth factor (PIGF), nerve growth factor (NGF), bone-derived growth factor (BDF), brain-derived neutrophic factor (BDNF), colony stimulation factor (CSF), and a combination thereof.

5. A wet dressing material for healing wounds comprising the composition of claim 4.

6. A wet dressing material for healing wounds comprising the composition of claim 3.

7. A composition comprising the glycol chitosan hydrogel according to claim 2 and a drug.

8. The composition according to claim 7, wherein the drug is a water-soluble drug.

9. The composition according to claim 8, wherein the water-soluble drug is a curcumin hydrophilized by using a beta-cyclodextrin.

10. A wet dressing material for healing wounds comprising the composition of claim 9.

11. A wet dressing material for healing wounds comprising the composition of claim 8.

12. A wet dressing material for healing wounds comprising the composition of claim 7.

13. A wet dressing material for healing wounds comprising the glycol chitosan hydrogel of claim 2.

14. A method for preparing a visible light-curable glycol chitosan of the following Formula 1 comprising reacting a glycol chitosan of Formula 2 sequentially with glycidyl methacrylate of Formula (i) and with polyethylene glycol-bis carboxylic acid of Formula (ii) according to Reaction Scheme 1 below:

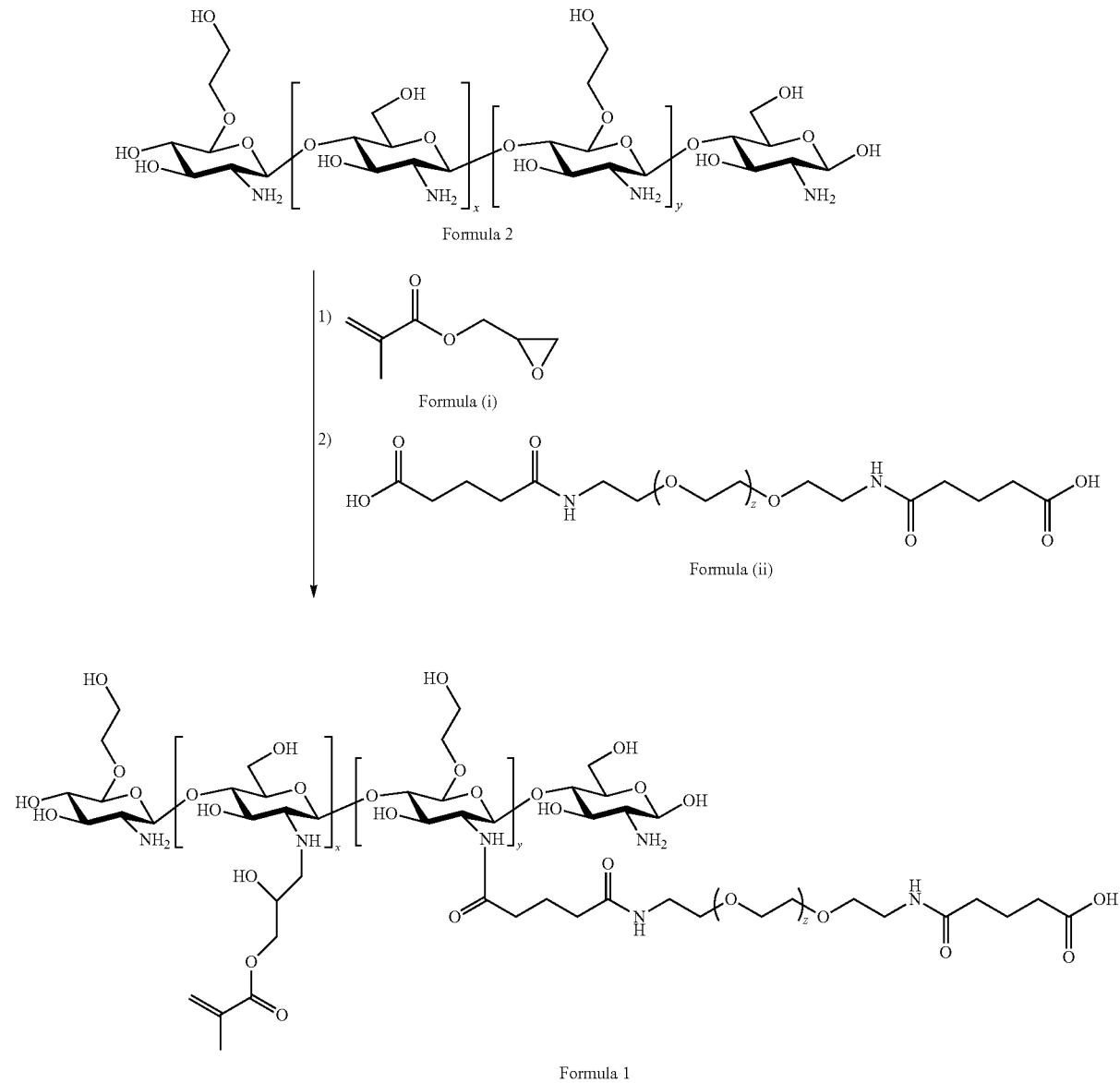

wherein x+y is an integer of 20 to 100 and z is an integer of 20 to 115; and wherein both x and y are greater than zero.

15. A method for preparing a glycol chitosan hydrogel comprising crosslinking a visible light-curable glycol chitosan of the following Formula 1 by visible light in the presence of a photo-initiator:

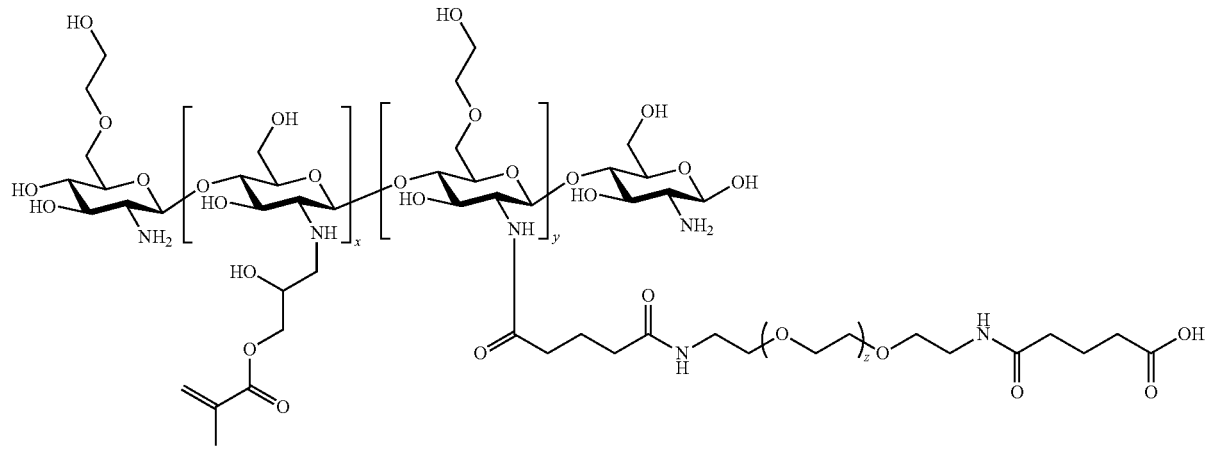

Formula 1 wherein x+y is an integer of 20 to 100, and z is an integer of 20 to 115; and wherein both x and y are greater than zero.

16. The method for preparing the glycol chitosan hydrogel according to claim 15, wherein the photo-initiator is riboflavin.

17. The method for preparing the glycol chitosan hydrogel according to claim 15, wherein the visible light is a visible light within a wavelength range of 435 to 480 nm.

* * * * *